United States Patent
Hansen et al.

(10) Patent No.: US 6,849,070 B1
(45) Date of Patent: Feb. 1, 2005

(54) CATHETER SET

(75) Inventors: Henrik Christian Hansen, Nivaa (DK); Allan Tanghoej, Kokkedal (DK); Niels Horsboel, Esbjerg (DK)

(73) Assignee: Coloplast A/S, Humblebaek (DK)

( * ) Notice: Subject to any disclaimer, the term of this patent is extended or adjusted under 35 U.S.C. 154(b) by 0 days.

(21) Appl. No.: 09/787,423

(22) PCT Filed: Sep. 23, 1999

(86) PCT No.: PCT/DK99/00501

§ 371 (c)(1),
(2), (4) Date: Mar. 23, 2001

(87) PCT Pub. No.: WO00/16843

PCT Pub. Date: Mar. 30, 2000

(30) Foreign Application Priority Data

Sep. 23, 1998 (DK) ........................ 1998 01196

(51) Int. Cl.[7] .............................................. A61M 27/00
(52) U.S. Cl. ..................................... 604/544; 604/328
(58) Field of Search ................................ 604/523–525, 604/528, 533, 544, 328, 264–265, 508; 206/363–364, 370, 438

(56) References Cited

U.S. PATENT DOCUMENTS

| | | | |
|---|---|---|---|
| 1,120,549 A | * 12/1914 | Schellberg | 604/171 |
| 2,856,932 A | 10/1958 | Griffitts | 128/294 |
| 3,537,451 A | * 11/1970 | Beck | 604/165.03 |
| 3,648,704 A | * 3/1972 | Jackson | 604/172 |
| 3,650,272 A | 3/1972 | Ericson | 128/275 |
| 3,750,875 A | * 8/1973 | Juster | 206/364 |
| 3,853,130 A | * 12/1974 | Sheridan | 604/171 |
| 3,865,165 A | 2/1975 | Glass | 150/1 |
| 3,934,721 A | * 1/1976 | Juster et al. | 206/364 |
| 4,062,363 A | * 12/1977 | Bonner, Jr. | 604/171 |
| 4,178,735 A | * 12/1979 | Jackson | 53/473 |
| 4,230,115 A | * 10/1980 | Walz et al. | 604/517 |
| 4,306,029 A | 12/1981 | Carpenter | 435/268 |
| 4,449,971 A | 5/1984 | Cawood | 604/54 |
| D311,064 S | * 10/1990 | Utas-Sjoberg | D9/414 |
| 5,147,341 A | 9/1992 | Starke et al. | 604/349 |
| 5,181,913 A | * 1/1993 | Erlich | 604/263 |
| 5,226,530 A | * 7/1993 | Golden | 206/210 |
| 5,454,798 A | * 10/1995 | Kubalak et al. | 604/328 |
| 6,053,905 A | * 4/2000 | Daignault et al. | 604/544 |

FOREIGN PATENT DOCUMENTS

| | | | |
|---|---|---|---|
| EP | 0 185 809 | 7/1986 | |
| EP | 0 334 509 | 9/1989 | |
| GB | 2 031 735 | 4/1980 | |
| GB | 2 033 231 | 5/1980 | |
| GB | 2 284 764 | 6/1995 | |
| HU | 214 735 | 7/1998 | |
| WO | 97/26937 | 7/1997 | |
| WO | 98/11932 | 3/1998 | |
| WO | WO 98/19729 | * 5/1998 | .......... A61M/25/00 |

* cited by examiner

*Primary Examiner*—Larry I. Schwartz
*Assistant Examiner*—Michele Kidwell
(74) *Attorney, Agent, or Firm*—Jacobson Holman PLLC

(57) ABSTRACT

A catheter se comprising a catheter and a package for storing of the catheter before use and for collecting or discharging urine, wherein an elongated part of the package forms a tube and wherein the catheter has a proximal part to be inserted into the urethra, a distal part in the form of a tubular section having an inner diameter at least as large as the inner diameter of the part of the proximal part of the catheter and a sealing part separating the proximal part of the catheter and the tubular distal part. The inventive shape of the catheter combined with the shape of the package prevents a blocking of the free flow of urine from the urethra into the package.

26 Claims, 4 Drawing Sheets

CATHETER SET

FIELD OF THE INVENTION

The present invention relates to a catheter set comprising a catheter and a package for both storing of the catheter before use and for collecting or discharging urine.

BACKGROUND OF THE INVENTION

Urinary catheter sets comprising a catheter having a hydrophilic coating, a wetting receptacle and a wetting fluid are disclosed in WO publication No. 98111932 (Coloplast A/S) and in WO publication no. 97126937 (Astra Aktiebolag).

Both publications describe catheter sets comprising both a catheter and a package, and in both publications an elongated part of the package forms a tube and is used for leading urine either to the inside of the package for later disposal or to an exterior container e.g. a toilet bowl for immediate disposal.

The use of such catheter sets is described by referring to FIG. 1 of WO 97/26937. First the proximal portion of the pocket 2 is torn off and the elongate shaft 18 of the catheter 3 is manoeuvred through the opening in the proximal end of the pocket 2 and into the urethra of the patient until a flared distal portion 16 forms a mechanical seal connection with the opening. Urine in the bladder of the patient is transported through the lumen of the catheter 3 into the urine collection chamber 12. After emptying the bladder the catheter 3 is manoeuvred back inside the bag 1 and the open end of the pocket 2 closed off for example by tying a knot with the material defining the pocket 2 or clamping the pocket with a clamp.

A disadvantage with these catheter sets is that the mechanical seal connection between the flared distal portion of the catheter and the proximal part of the package does not always work properly and the result is that urine flows backward and out of the package, especially due to restriction of the flow from the catheter into the receptacle due to folding, twisting or kinking of the elongate part of the device leading from the catheter to the receptacle.

GB 2031735 discloses a catheter set comprising a catheter within a package for collecting urine. So does GB 2284764, GB 2033231 and U.S. Pat. No. 5,147,341. The rearward end of these catheters are either flared outwardly or provided with an arresting member to keep the catheter from leaving the package unintendedly. Non of these references provides an elongated part of the package to serve as a wetting receptacle for wetting the catheter.

U.S. Pat. No. 2,856,932 discloses a catheter set comprising a catheter and a package having an elongated part covering part of the catheter to assist insertion of the catheter in a non-contaminating manner. At the rearward end of the catheter it is flared outwardly to keep the catheter in place in relation to the package during use. This shape of entrance into the package provides the same disadvantages and risks of flow restriction as mentioned above due to possible occurrence of twisting or kinking at the link between the elongated and the broader part of the package. Furthermore a considerable length of the catheter is "inactivated" by not being able to leave the elongated neck and such extra length would have to be added to the catheter in addition to the necessary "active length" causing considerable extra costs. For short catheters this extra length constitutes a considerable part of the total length of the catheter.

The object of the invention is to solve this problem and provide a catheter set preventing the risk of spilling urine over cloth or surroundings when performing intermitting catherisation, especially when performed by the patient him-/herself, and at the same time to provide a catheter set which is simple and inexpensive to produce. It has surprisingly been found that the above drawbacks may be overcome using a catheter set according to the invention.

BRIEF DESCRIPTION OF THE INVENTION

The present invention relates to a catheter set comprising a catheter and a package for both storing of the catheter before use and for collecting or discharging urine. The inventive shape of the catheter combined with the shape of the package prevents blocking of the free flow of urine from the urethra into the package during use by securing the relatively soft and pliable package from kinking or squeezing.

BRIEF DESCRIPTION OF THE DRAWINGS

The invention will be explained more in detail with reference to the accompanying drawings showing embodiments of the invention and in FIG. 1 shows an embodiment of a catheter set according to the invention, FIG. 5 shows the embodiment of FIG. 3 in a sealed state.

DETAILED DESCRIPTION OF THE INVENTION

Figure 1:
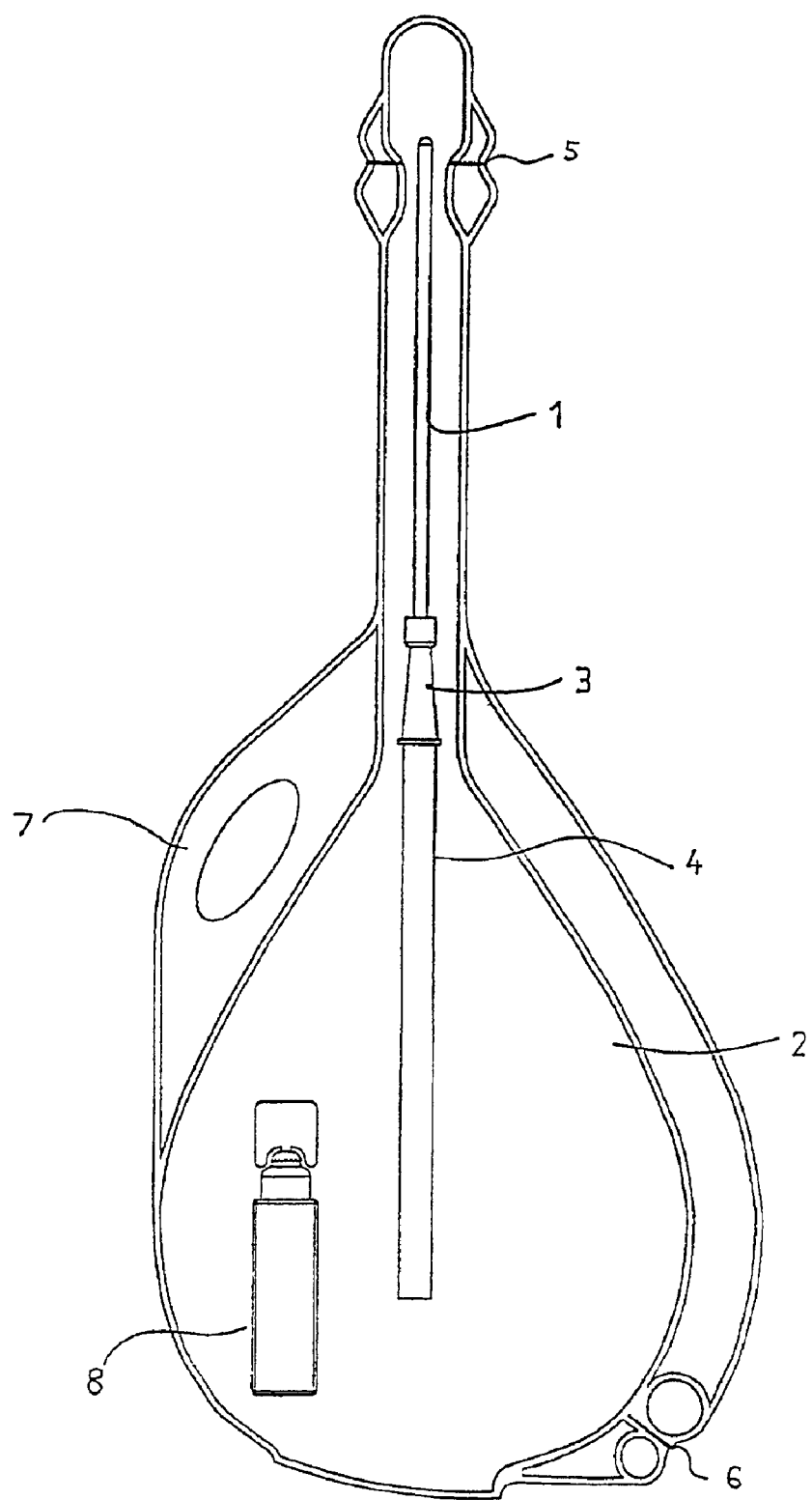

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The present invention relates to a catheter set comprising a catheter and a package for storing of the catheter before use and for collecting or discharging urine, wherein an elongated part of the package forms a tube for accommodating the catheter. The catheter comprises a proximal part to be inserted into the urethra and a distal part in the form of a tubular section having an inner diameter at least as large as the inner diameter of the proximal part of the catheter, and a sealing part separating the proximal part of the catheter and the tubular distal part. The length of the tubular distal part is at least long enough to occupy the length of the elongated part of the package such that, in use, the tubular distal part is present in the elongated part of the package.

The sealing part may e.g. be a part of the catheter having an increased diameter. Such a sealing part will also function as a stop preventing the catheter from falling out of the package and, at the same time function as a seal during use preventing spilling of urine during catherisation.

The proximal part of the catheter will usually have an essentially uniform thickness of material as will the distal part.

It is very practical when the sealing part is separating the proximal part of the catheter and the tubular distal part as this provides safety against trying to insert the tubular part into the urethra and also ensures that the tubular part remains in the package for ensuring the free flow of urine into the package.

When in use, the distal tubular part of the catheter of the invention reaches into the upper part of the package and keeps the front and rear parts thereof apart and thus prevents a blocking of the free flow of urine from the urethra into the package. Thus the length of the tubular distal part of the catheter is at least as long as the length of the elongated part of the package. In the absence of the tubular part, urine flowing through the catheter may meet an obstacle if for example the package is folded or squeezed and thus, the urine will fill up the upper part of the package and establish a back pressure on the sealing between the catheter and the package. When a tubular part of the catheter is inside the package as an extension of the catheter it thus prevents the flow of urine from being disturbed in the upper part of the relatively soft package, and the flow of urine will be directed downwards until the package is full. The inner diameter of the tubular part of the catheter must be of at least of the same dimension as the proximal part of the in order not to hamper the free flow of urine from the bladder through the catheter and into the package. Thus the inventive shape of the catheter in combination with the shape of the package prevents a blocking of the free flow of urine form urethra into the package.

The tubular part of the catheter may be a prolonged part of the catheter itself or a separate tubular piece which is connected to the catheter.

In a preferred embodiment of the invention the proximal part of the catheter has a hydrophilic coating. A hydrophilic coating may be any hydrophilic coating known per se for use for hydrophilic coated catheters and the coating may be applied using any method known per se for applying a hydrophilic coating to a catheter.

The catheter set according to the invention preferably comprises a wetting fluid integrated into the package in order to enable activation of a hydrophilic coating irrespectively of the access to pure water. The wetting fluid may be sterilised water or saline.

The elongated shape of part of the package is especially useful when the catheter has a hydrophilic coating of the type needing activation by addition of wetting fluid. When the elongated part of the package accommodates the catheter—at least during the wetting process, but preferably already when package is produced and packed ready for sale—the amount of wetting fluid needed to ensure proper wetting is drastically reduced compared to the amount needed if wetting was to take place in the wider part of a package.

It is understood that the location of the catheter in the elongated part can take place already when the package is produced. But also the package can be produced with the catheter situated inside the broader part of the package in which situation the catheter is introduced into the elongated part of the package at any time prior to use to let the elongated part of the package accommodate the catheter.

In one embodiment of the invention the tubular distal part of the catheter has an inner diameter larger than the inner diameter of the proximal part of the catheter. Thus, no extra resistance against the flow will occur and, as the outer diameter thereof is consequently also greater, the transition between the two parts of the catheter may function as a stop and sealing.

The tubular part of a catheter is preferably made from an extrudable, mouldable material such as a polyolefin such as polyethylene (PE) or polypropylene (PP) or a copolymer of polyethylene such as ethylene vinyl acetate (EVA) or polyvinyl chloride (PVC) or polyvinylidene chloride or a polyurethane (PU) or a silicone. It is envisaged that the proximal and distal tubular part of the catheter and the sealing part may be produced as an integrated unit from the same material by a combination of injection moulding, extrusion and/or blowing.

It is preferred when the tubular distal part of the catheter is transversely corrugated as this adds to the security against kinking: A suitable flexible and transversely corrugated tube is known per se for preventing blocking by bending of the tube leading to urine collection bags.

In accordance with a preferred embodiment of the catheter set of the invention the package includes an elongated narrow part designed for accommodating the catheter at least during wetting of the catheter and for the exit of the catheter during use.

In this embodiment the tubular part of the catheter may e.g. be in the form of a telescopically extendible tube having a maximum diameter grater than the proximal part of the catheter. Alternatively the tubular part may be in the form of an extendible corrugated tubing resembling a corrugated straw which may be folded, compressed or stretched like an accordion. This embodiment can advantegeously be used when the urine is led directly to an exterior container e.g. a toilet bowl.

In accordance with another preferred embodiment the package also includes a broader container part for collecting the urine. In accordance with yet another preferred embodiment of the invention the package is provided with one or more sealing devices on the exterior side of the package designed for holding and sealing the elongated end of the package after use. When using the package for collecting urine, it is possible to tie a knot on the elongated part after pushing the catheter into the package but this still leaves a small amount of urine in the outer part of the package which may be spilled onto the clothes which will be embarrassing for the user.

The sealing device is preferably in the form of an adhesive sheet adhered to the package. The sheet may typically comprise a sheet of a relatively soft and pliable material having an adhesive on the surface facing the outer side of the package and wherein a part of this surface is covered with a release liner which is adhered to the outer surface of the package. Thus, the sheet functions as a part of the surface of the package when not in use, and when used, the sheet is released from the release liner, which is then removed, ant the top of the bag is preferably placed at the adhesive area and the sheet is placed at the adhesive area holding and sealing the end of the bag.

The sealing device of this embodiment securely doses and seals the opening of the package and furthermore, it enables a sealing by bending the top of the package and securing and sealing the same below a flap of an adhesive sheet adhered to the package the sealing device without having to push the catheter into the package which facilitates the sealing and provides a better security against spilling of urine.

The sheet may be of any suitable material e.g. the ones mentioned above. The adhesive may be any suitable adhesive being compatible with the package material and the sheet material. It is preferred when the adhesive exhibit some moisture absorbing capability in order to ensure a secure sealing even if some drops of urine are spilled when sealing the top of the package after use. An moisture absorbing adhesive may be any such adhesive known per se for wound or ostomy purposes, e.g. containing hydrocolloids.

A release liner may for instance be siliconized paper.

The package may be made from a water impervious layer or film of any suitable material known per se for use in the preparation of urine collection bags.

The length of the tubular part may vary according to the specific application. Of course, it should not be so long that it cannot be comprised in the bag. Even at small lengths of the tubular part an effect is obtained. In a preferred embodiment the tubular part has a length at least corresponding to the narrow upper part of the package.

DETAILED DESCRIPTION OF DRAWINGS

Reference is made to FIG. 1. The embodiment of the catheter set of the invention shown in FIG. 1 comprises a catheter 1, a package 2 for collection of urine, a sealing part 3 and a flexible tubular part 4 connected to the catheter 1. The top of the package is easily torn off at 5 being a weak point for breaking the package. Furthermore, the package comprises another weak point 6 designed for opening the package at the distal end, if desired, during use, if the package is to function as guide to e.g. a toilet bowl or after use if it is desired to empty the bag immediately. The package is shown with an ear 7 for an easy handling of the package during and after use. Furthermore, a container 8 is shown comprising a wetting fluid.

Figure 2:
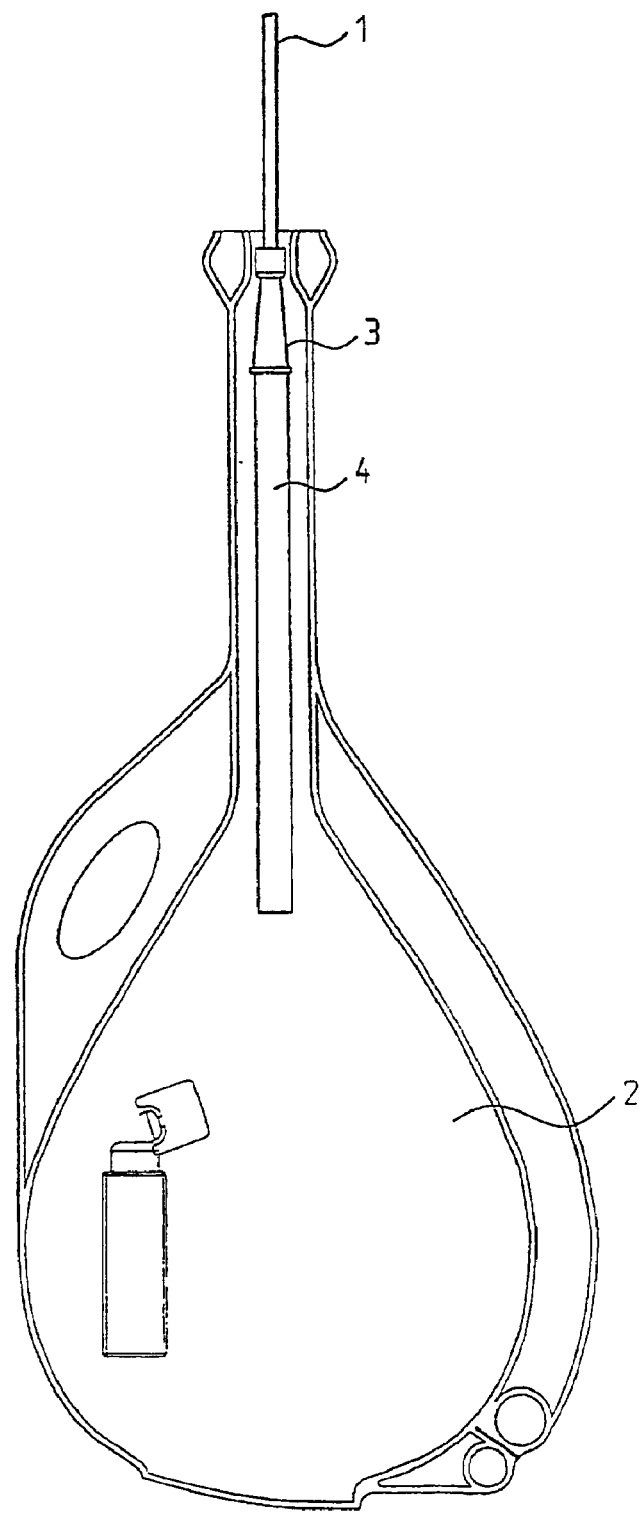
FIG. 2 shows the embodiment of FIG. 1 ready for use.

In FIG. 2 the embodiment of FIG. 1 is shown after opening the container and wetting the catheter and tearing off the top of the package and pushing the catheter until the stop engages with the bag ready for insertion. The insertion may, if desired, be performed concomitantly with the pushing out of the catheter.

Especially in the case where the catheter is of the hydrophilic coated type the catheter can be wetted to activate the hydrophilic coating prior to tearing off the top of the package at the weak point 5 and inserting the catheter into urethra. While accommodated in the elongated part of the package the catheter is thus surrounded by the wetting fluid of the container 8 after breaking off the tip of that container and holding the package so that the elongated part of the package points essentially downwards to ease the transportation of wetting fluid by gravity down into the elongated part of the package.

When the catheter is in use the urine flows in through the openings in the upper part—the proximal end—of the catheter 1 and enters the inside of the package 2 where it passes through the upper part which, in this embodiment, is in the form of a narrow portion as compared to the lower part of the package which is formed as a broader collection part. When the urine is passing the upper part of the package 2 it also passes the flexible tubular part 4 which is present inside this part of the package and secured to the catheter 1. The flexible tube 4 provides the package with a certain stiffness which prevents blocking of this part by kinking or squeezing of the relatively soft and pliable package 2. In the figure the flexible tube is shown as a smooth tube but it might as well have a corrugated surface. The most important features for the tube is that it has to be both bendable and in possession of a certain stiffness.

When the user has finished the use of the catheter he can either throw the used catheter and the filled or urine contaminated package away immediately or he can close the package and transport it to the nearest convenient waste container if there are not any present at the facility.

The user might experience a problem trying to close the package of the catheter set according to the invention as it is difficult to force the catheter down into the lower part of the package especially when the user has reduced motility of the hands, and when the catheter is still present in the narrow part of the package it is almost impossible for the user to tie a liquid-tight knot on the narrow part as recommended in the instructions for use of Convene EasiCath Set from Coloplast A/S.

Figure 3:
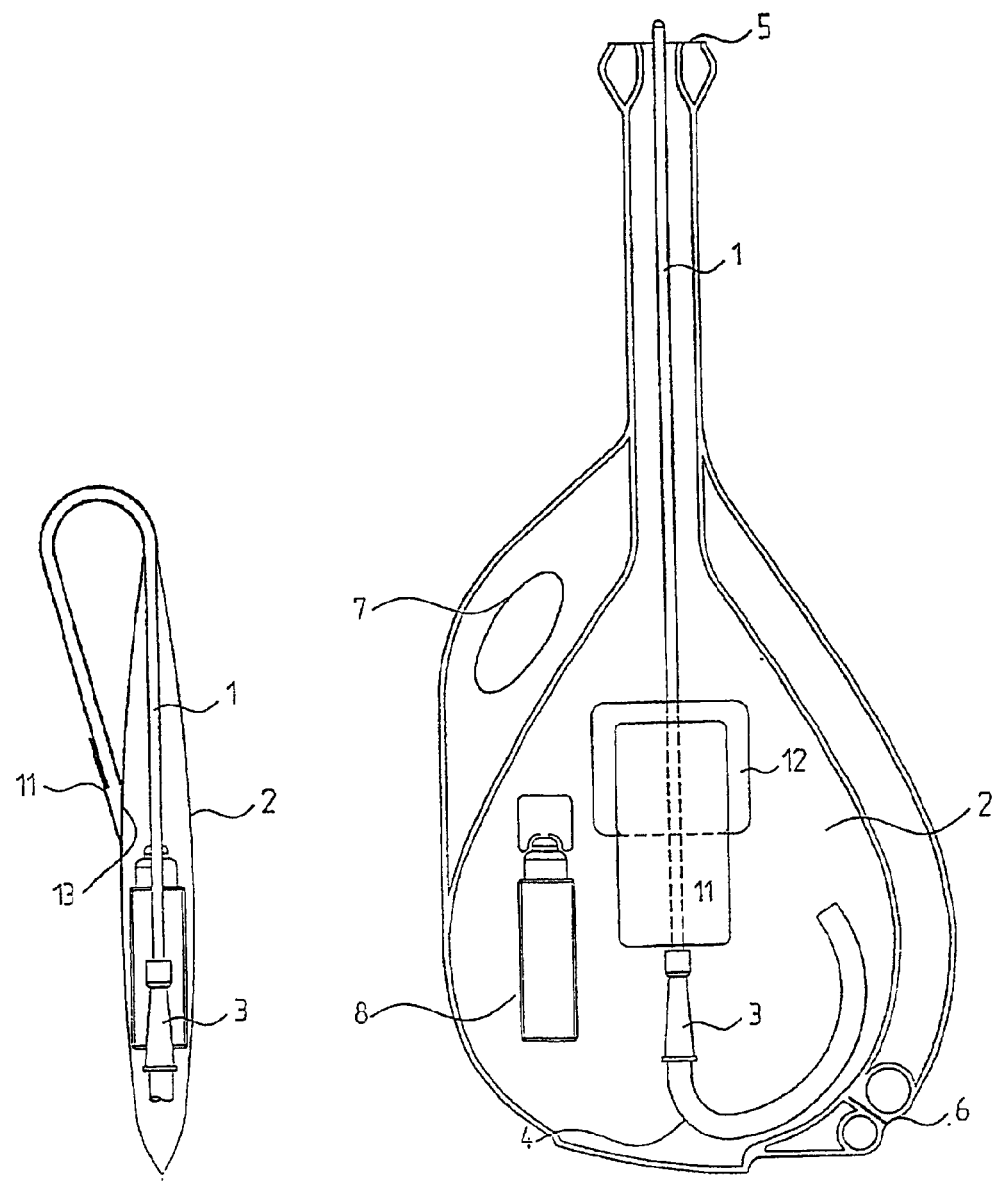
FIG. 3 shows another embodiment of a catheter set according to the invention.

Reference is made to FIG. 3 showing an embodiment of the package of the invention having a sealing device at the exterior side of the package. In order to solve the above problem and render it easier for the user to transport a filled package it is preferred to use a different kind of closing system as e.g. a system where the upper end of the catheter set package is closed with a piece of gummed tape or tied together by extra added parts.

Figure 4:
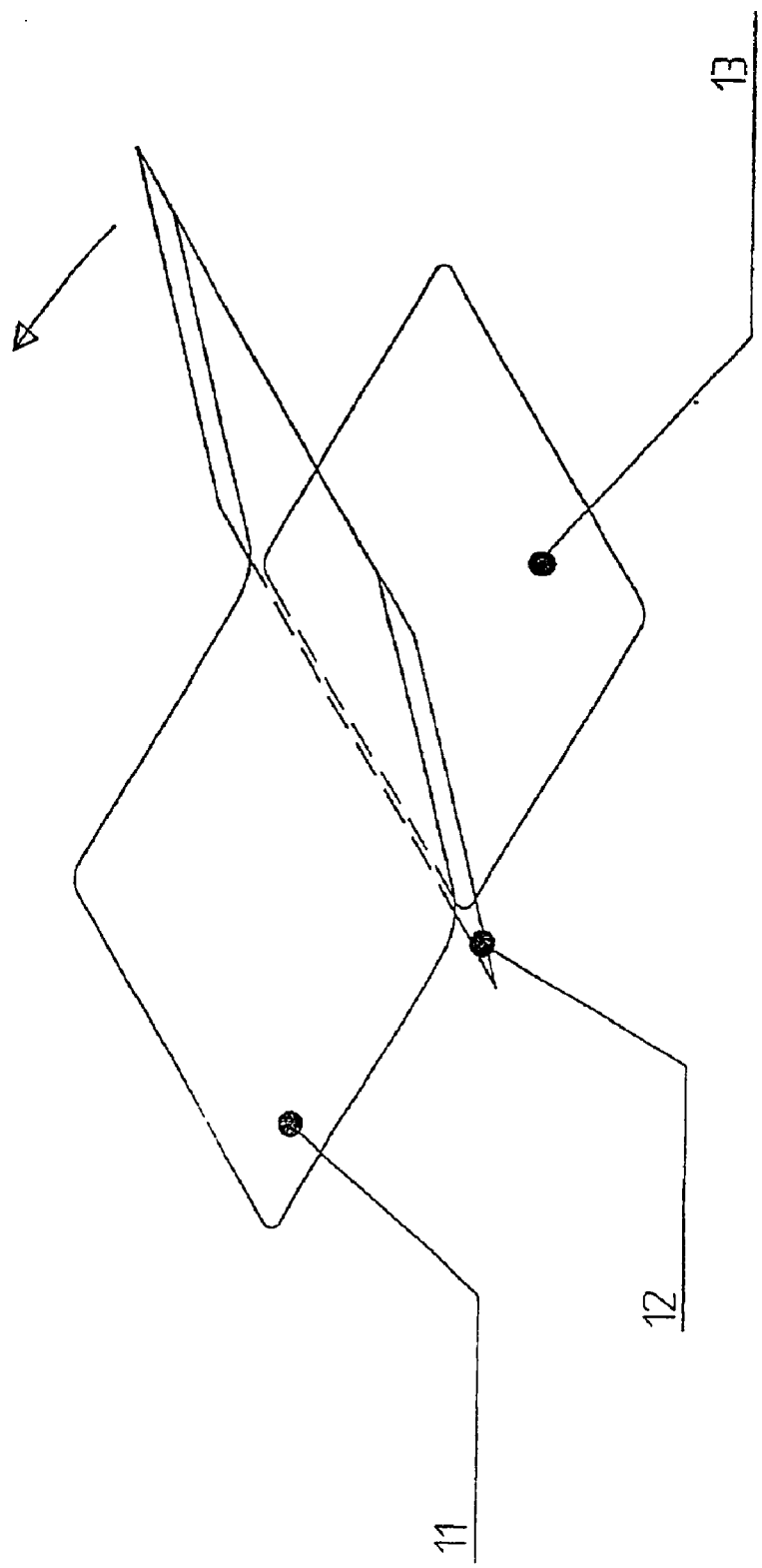
FIG. 4 shows a sealing system according to the invention in an enlarged scale.

A very effective sealing device comprises three pieces of film or paper and is illustrated in FIGS. 3–5. FIG. 4 shows how the three pieces are arranged in connection with each other: an upper piece 11, a middle piece 12 and a lower piece 13. The upper piece is non-adhesive on the outer surface and adhesive on the surface facing the package, one end of this piece is adhered to the package and the other end is adhered to the middle piece 12. The middle piece 12 is non-adhesive on both surfaces and both surfaces are made of a material which makes it possible to release it from adhesive surfaces without spoiling the adhesiveness. The middle piece 12 is preferably considerably larger than the one end of the upper piece 11 it is covering as this makes it easier to grab and remove the middle piece 12 from the package. The middle piece may e.g. be made from siliconised paper. The surface of the middle piece facing 12 away from the upper piece 11 is facing the lower piece 13. The lower piece 13 is adhesive on both surfaces, one surface secure the lower piece 13 to the package and the other surface secure the lower piece 13 to the middle piece 12.

Before the closing device is used for securing and sealing the proximal end of the catheter set, the three pieces are placed on the front or the backside of the package, they are all three releasably glued together as each of them get contact with at least one adhesive surface. When the user need to close the package he pulls the middle piece 12 and the upper end of the upper piece 11 backwards, by this action the middle piece 12 is released from the lower piece 13 (only the movement of the upper piece 11 is indicated in the figure). After the user has remove the middle piece 12 from the upper piece 11, the user places the open end of the catheter set on the lower piece, this will secure the position of the open end, and then the user covers the open end of the package with the upper piece. The open end of the package is now secured between the upper and the lower piece.

FIG. 5 shows a sectional view of a package with the sealing device in a closed position.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A catheter set comprising a catheter and a package for storing of the catheter before use and for collecting or discharging urine, said package including an elongated, narrow part forming a tube for accommodation of a proximal part of the catheter, and a broader container part, the proximal part of the catheter having an inner diameter and being adapted to be inserted into the urethra, said catheter including a sealing part providing a seal between the catheter and the elongated part of the package which prevents passage of urine through said tube except through said catheter inner diameter during use, and further including a distal part formed as a tubular section having an inner diameter at least as large as the inner diameter of the proximal part of the catheter, said sealing part separating the proximal part of the catheter and the tubular distal part, and a length of the tubular distal part being at least as long as a length of the elongated, narrow part of the package such that, in use, the tubular distal part is present within and extends through the length of said elongated, narrow part.

2. The catheter set according to claim 1, wherein the proximal part of the catheter has a hydrophilic coating.

3. The catheter set according to claim 1, wherein the set includes a wetting fluid integrated into the package.

4. The catheter set according to claim 1, wherein the tubular distal part of the catheter has an inner diameter larger than the inner diameter of the proximal part of the catheter.

5. The catheter set according to claim 1, wherein the tubular distal part is made from an extrudable, mouldable material.

6. The catheter set according to claim 1, wherein the tubular distal part of the catheter is transversely corrugated.

7. The catheter set according to claim 1, wherein the elongated narrow part is at an end of the package from which the catheter exits during use.

8. The catheter set according to claim 1, wherein the package is provided with at least one sealing device on an exterior side of the package.

9. The catheter set according to claim 8, wherein the sealing device includes an adhesive sheet adhered to the package.

10. The catheter set according to claim 5, wherein said extrudable, mouldable material is selected from the group consisting of polyolefins and copolymers of polyethylene.

11. A catheter set comprising a catheter and a package for storing of the catheter before use and for collecting or discharging urine, said package including an elongated part forming a tube for accommodation of a proximal part of the catheter which is adapted to be inserted into the urethra, said catheter including a tubular distal part and a sealing part for providing a seal between the catheter and the elongated part of the package during use, said sealing part separating the proximal and distal parts of the catheter at a fixed location thereon, a length of the tubular distal part being at least as long as a length of the elongated part of the package such that, in use, the tubular distal part is present within and extends through the length of said elongated part.

12. The catheter set according to claim 11, wherein the proximal part of the catheter has a hydrophilic coating.

13. The catheter set according to claim 11, wherein the set includes a wetting fluid integrated into the package.

14. The catheter set according to claim 11, wherein the tubular distal part of the catheter has an inner diameter at least as large as an inner diameter of the proximal part of the catheter.

15. The catheter set according to claim 11, wherein the tubular distal part of the catheter has an inner diameter larger than an inner diameter of the proximal part of the catheter.

16. The catheter set according to claim 11, wherein the tubular distal part is made from an extrudable, mouldable material.

17. The catheter set according to claim 11, wherein the tubular distal part of the catheter is transversely corrugated.

18. The catheter set according to claim 11, wherein the tubular distal part is flexible but has sufficient stiffness to prevent kinking of said elongated part.

19. The catheter set according to claim 11, wherein the package is provided with at least one sealing device on an exterior side of the package.

20. The catheter set according to claim 19, wherein the sealing device includes an adhesive sheet adhered to the package.

21. The catheter set according to claim 1, wherein said sealing part separates said proximal and distal parts of the catheter at a fixed location thereon.

22. The catheter set according to claim 1, wherein an exterior opening of said elongated narrow portion is concurrent with an open edge of said package, said seal being adjacent said exterior opening.

23. The catheter set according to claim 1, wherein said proximal, distal and said sealing parts are produced together as an integrated unit.

24. The catheter set according to claim 1, wherein said tubular part is a separate piece connected to said catheter via said sealing part.

25. The catheter set according to claim 11, wherein said seal formed by said sealing part prevents passage of urine though said tube except through an inner diameter of said catheter.

26. The catheter set according to claim 11, wherein an exterior opening of said elongated narrow portion is concurrent with an open edge of said package, said seal being adjacent said exterior opening.

* * * * *